Figure 1:
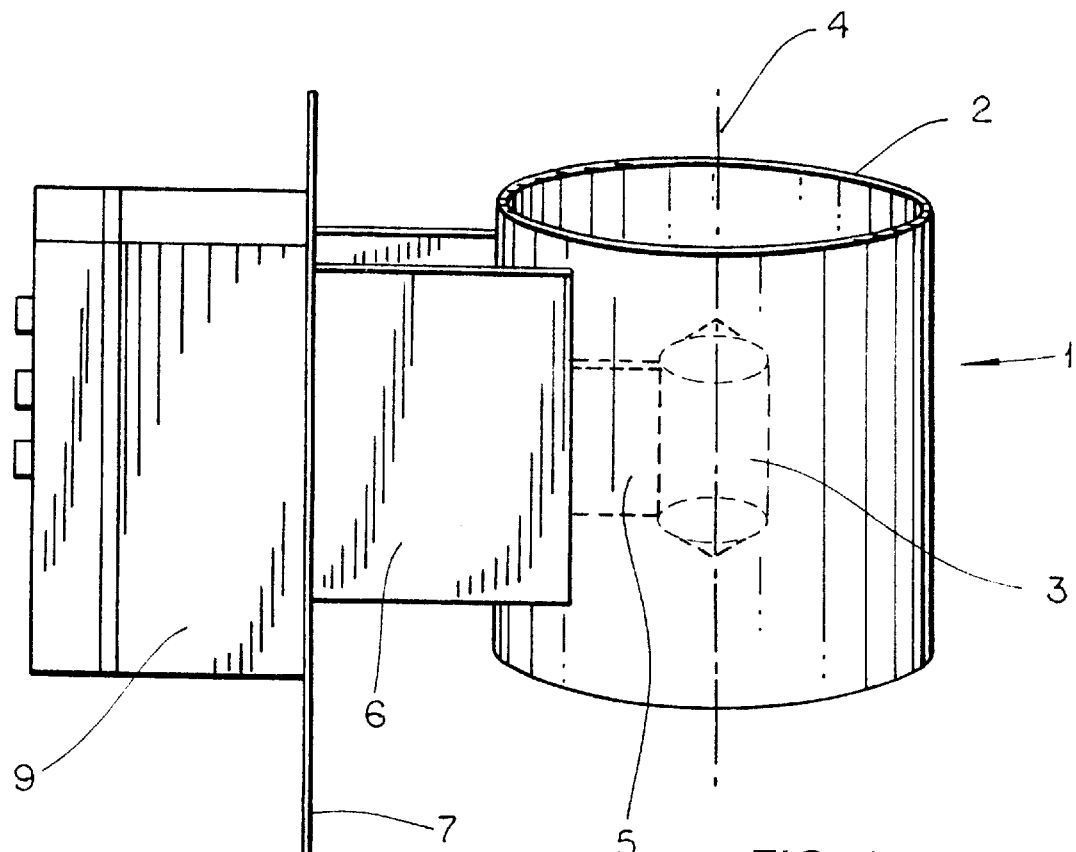

United States Patent [19]
Larsen

[11] Patent Number: 5,852,368
[45] Date of Patent: Dec. 22, 1998

[54] SENSOR FOR THE MEASUREMENT OF MOISTURE IN A FLOW OF MATERIAL

[76] Inventor: Ebbe Busch Larsen, DK-5230, Odense M, Denmark

[21] Appl. No.: 775,013

[22] Filed: Dec. 27, 1996

[51] Int. Cl.[6] .................................................... G01N 27/22
[52] U.S. Cl. .......................... 324/689; 324/690; 324/695; 324/696; 361/285; 361/286
[58] Field of Search ..................... 324/689, 690, 324/695, 696; 361/285, 286

[56] References Cited

U.S. PATENT DOCUMENTS

| | | | |
|---|---|---|---|
| 3,078,709 | 2/1963 | Clark | 324/690 |
| 3,665,301 | 5/1972 | Maltby | 324/690 |
| 4,075,680 | 2/1978 | Shipp | 324/690 |
| 4,547,725 | 10/1985 | Oetiker | 324/665 |
| 5,249,455 | 10/1993 | Cox | 324/689 |

FOREIGN PATENT DOCUMENTS

| | | | |
|---|---|---|---|
| 1427818 | 1/1966 | France | 324/689 |
| 1437764 | 11/1988 | U.S.S.R. | 324/689 |

Primary Examiner—Ernest F. Karlsen
Assistant Examiner—Jose M. Solis
Attorney, Agent, or Firm—Nims, Howes, Collison, Hansen & Lackert

[57] ABSTRACT

A sensor for the measurement of moisture in a flow of material, especially loose material such as meal material, grains, granulates and similar materials which are to be pressed to form feed pills in presses. The sensor comprises a tube piece of an electrically conductive material with circular cross-section, and an elongated pole which is of circular cross-section and is disposed with its longitudinal axis concentrically and electrically insulated in the tube piece, and which consists of an electrically conductive material. When the moist material flows between the inside surface of the tube piece and the outer side of the pole, the sensor works with the moist material's conductivity as a condenser for the capacitive detection of the moistness, which can be determined on the basis of the detection.

5 Claims, 2 Drawing Sheets

SENSOR FOR THE MEASUREMENT OF MOISTURE IN A FLOW OF MATERIAL

This invention concerns a sensor for the measurement of moisture in a flow of material, especially loose material such as meal material, grains, granulates and similar materials which are to be pressed into feed pills in presses, in connection with pre-processing such as the extrusion of feedstuffs, and for the measuring of a finished product, regardless of whether this is pelleted or extruded.

It is difficult to pump materials of this kind, in that they are inclined to hang together in clumps, whereby the material progresses in a spasmodic manner, which results in great measurement inaccuracies due to the uneven, pulsating feeding forward.

In the production of feed pills, the moisture content in the material is of decisive importance for the quality of the finished feed pills produced from the above-mentioned materials.

It is therefore the object of the present invention to provide a sensor which is capable of measuring the content of moisture in a flowing material with great accuracy, even though the material is possibly fed forward in a pulsating stream, so that the production of feed pills can be controlled very accurately with the object of optimizing the quality of the feed pills.

This object is achieved with a sensor of the kind disclosed in the preamble, said sensor being characterized in that the sensor comprises a tube piece of electrically conductive material with circular cross-section, and an elongated pole which has a circular cross-section and is disposed with its longitudinal axis concentrically and electrically insulated in the tube piece, and which consists of an electrically conductive material.

The sensor according to the invention, which is based on the capacitive measuring principle, can be placed in the flow of material in which the content of moisture is to be measured, regardless of whether the material is fed forward in an even or a pulsating stream.

The capacitive measuring principle is based on the dielectrical characteristics of the material in which the moistness is to be measured, i.e. the ability of the material to conduct an electric current. In principle, the sensor is a condenser with two measurement surfaces between which the material is fed during the measurement.

A condenser's characteristics depend on:

a) the distance between the electrodes, b) the area of the electrodes, and c) the dielectricity between the electrodes.

The distance between the electrodes of the sensor according to the invention is constant, and the area of said electrodes is also constant. Consequently, the only factor that can vary with the sensor is the dielectrical characteristics of the material which is to be measured for moistness.

With the object of easing the flow of material past the pole, the ends of the elongated pole are conical.

The surface of the elongated pole has a coating, such as fibre-glass or the like, which is suitable for reducing the friction between the material and the surface of the pole.

Since the temperature of the flowing material in which the moisture is to be measured is of significance for the conductivity of the material, a temperature sensor is provided inside the elongated pole.

The tube piece and the pole disposed herein can form part of a bridge, where the conductivity in the bridge constitutes a capacitance, and where a difference in the conductivity is detected and measured, i.e. the higher the conductivity the greater the moistness, and the lower the conductivity the lower the moistness.

Figure 2:
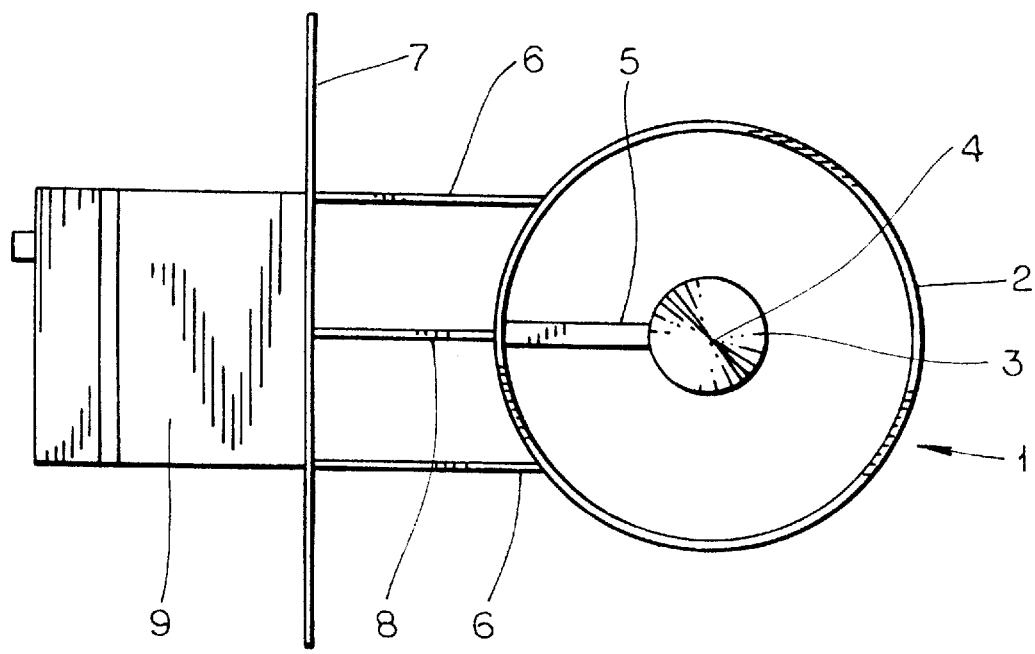
Figure 3:
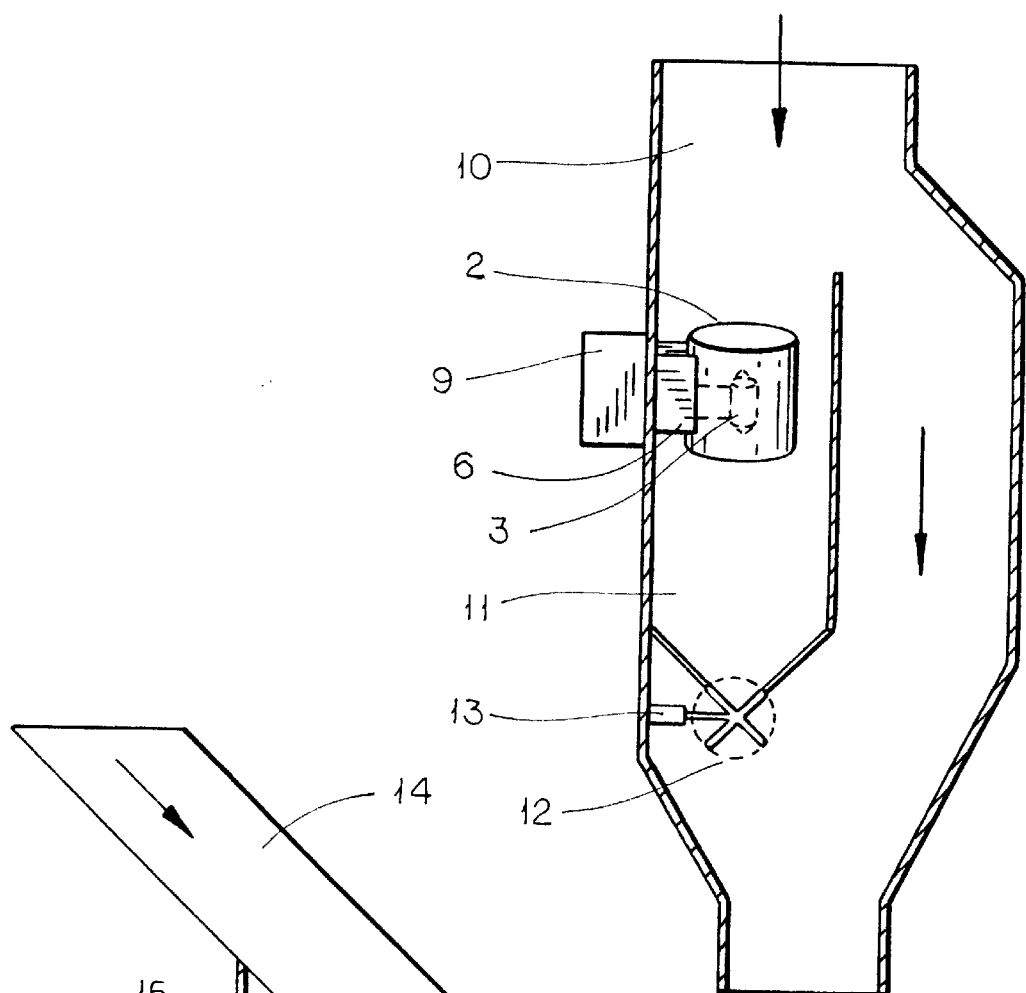
Figure 4:
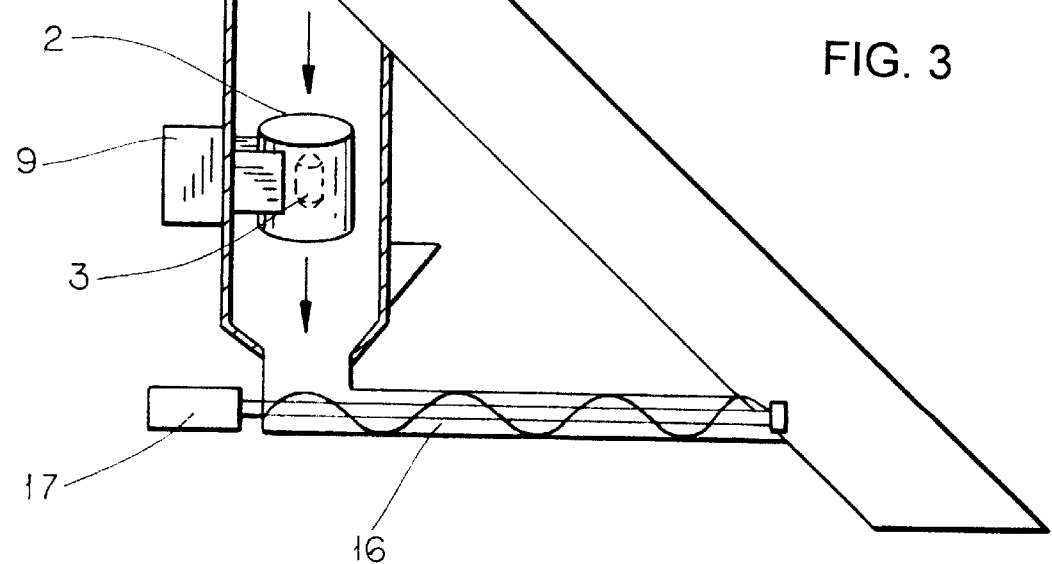

The sensor according to the invention is explained in more detail in the following with reference to the drawing, where FIG. 1 shows in perspective a sensor according to the invention in a housing for the formation of a unit for mounting in a measuring chamber, FIG. 2 shows a cross-section of the sensor depicted in FIG. 1 and with the housing with which the sensor is connected, FIG. 3 shows a longitudinal section through a pipe for the feeding of a flowing material in which the moistness is to be measured, and in which pipe there is arranged a measuring chamber equipped with a sensor according to FIG. 1, FIG. 4 shows a pipe for the feeding of a flowing material in which the moistness is to be measured, and a longitudinal section in a side branch connected to the pipe equipped with a sensor according to FIG. 1.

FIG. 1 shows in perspective a sensor 1 according to the invention which comprises a tube piece 2 with circular cross-section and which is made of an electrically conductive material, such as stainless steel. Inside the tube piece 2 there is placed an elongated pole 3 which has a circular cross-section and which is placed with its longitudinal axis 4 concentrically and electrically insulated in the tube piece 2, and which consists of an electrically conductive material, for example stainless steel.

It will be understood that the radial distance between the pole 3 and the inner side of the tube piece 2 is of the same magnitude in all directions, and that the area of the electrodes is constant.

The pole 3 is mounted in the tube piece 2 by means of a spacing element 5, which in a manner not shown in detail is secured to the inner side of the tube piece 2. The spacing element 5 is made of an electrically insulating material having an outside surface which preferably has great wearing qualities.

By means of two support pieces 6, the tube piece 2 is connected to a mounting flange 7 which serves to position the sensor 1 in a place of use. Therefore, the mounting flange 7 is provided with suitable holes (not shown in the drawing) for screws or similar securing elements.

An electrical conductor 8 leads the current from the pole 3 through the spacing element 5 and further through a hole in the mounting flange 7 to a housing 9 disposed on the opposite side of the mounting flange 7, said housing containing elements for the processing of differences in electrical potential which can arise between the tube piece 2 and the pole 3. The hole in the mounting flange 7 is of such a diameter that the conductor 8 is electrically insulated from the mounting flange 7.

Together with the elements which are placed in the housing 9, the tube piece 2 with its support pieces 6 and the pole 3 with the conductor 8 form part of a bridge which can measure the conductivity in a moist material which is fed through the tube 2 between the inside surface of said tube and the pole 3.

The bridge thus constitutes an oscillatory circuit in which the material to be measured for moistness forms part with a given capacitance which can be measured and herewith indicate the value of the moisture content. The higher the conductivity the greater the moistness, and the lower the conductivity the lower the moistness.

With the object of easing the flow of material past the pole 3, the ends of the elongated pole 3 are made conical or spherical.

The surface of the elongated pole 3 has a coating, such as fibre-glass or the like, which is suitable for reducing the friction between the material and the pole 3. The coating also serves to reduce the risk of condensation of water, because this will otherwise give rise to a short-circuit between the tube piece 2 and the pole 3, and herewith render the measurement of the content of moisture in the material impossible.

Since the temperature of the flowing material in which the moisture is to be measured is of significance for the material's conductivity, a temperature sensor, which is not shown in the drawing, is provided inside the elongated pole 3.

In a first embodiment, which is shown in FIG. 3, the material in which the moisture is to be measured is fed through a pipe 10, and the sensor 1 is placed in a measuring chamber 11 in which a stowage of the material takes place, in that the measuring chamber 11 is restricted by a sluice which, for example, can be in the form of a mill-wheel with, for example, four arms, which in a controlled manner lead out a suitable amount of material at a time. The mill-wheel 12 is rotated by means of a mechanism 13 which, after a measurement, turns the next arm forward for the blocking of a new portion, while the portion of material measured is led further through the pipe 10. The flowing material hereby attains a uniform concentration which results in a greater accuracy in the measurement of the moisture content.

In a second embodiment, which is shown in FIG. 4, the flowing material in which the moisture is to be measured is fed through a pipe 14. A part of the material is diverted through a side branch 15 in which the sensor 1 is mounted. The lowermost end of the side branch 15 is closed by a worm conveyor 16 which is rotated in an intermittent manner by a motor 17, so that after a short period in the side branch the material is led back to the pipe 14.

The short period for which the material is in the side branch and herewith in the sensor 1 provides the possibility of obtaining an accurate determination of the content of moisture in the flowing material.

The results of the measurements which arise through the elements which are placed in the housing 9 are hereafter utilized for a continuous adjustment of the content of moisture in the flowing material, this being with the object of optimizing the quality of the finished feed pills, said optimization also being effected on the basis of the temperature which is measured with the temperature sensor provided in the pole 3.

I claim:

1. A sensor for the measurement of moisture in a flow of loose granular material comprising a tube piece of electrically conductive material with a circular cross-section, an elongated pole being electrically insulated and having a circular cross-section positioned with its longitudinal axis concentrically in the tube piece, the pole being made of an electrically conductive material, the tube piece connected via two support pieces to a mounting flange, a spacing element made of an electrically insulating material which is secured to the inner side of the tube piece, for mounting the pole in the tube piece, an outside surface of the spacing element having a high degree of wear resistance, a conductor extending from the pole through the spacing element and the mounting flange, being insulated thereby, the ends of the elongated pole being conical, and an outside surface of the elongated pole having a coating thereon for reducing condensation.

2. Sensor according to claim 1, characterized in that a temperature sensor is provided inside the elongated pole.

3. Sensor according to claim 1, characterized in that the sensor is configured to form part of a conductive bridge, where a difference in the conductivity can be detected and measured.

4. Sensor according to claim 1, characterized in that the sensor is configured to be placed in a measuring chamber which is inserted in a pipe for a flowing material in which the moistness is to be measured, said measuring chamber being restricted by a mill-wheel with four arms which, by intermittent rotation via a mechanism, in a controlled manner leads out portions of the material in which the moistness is to be measured.

5. Sensor according to claim 1, characterized in that the sensor is configured to be placed in a measuring chamber which is inserted in a side branch in a pipe for a flowing material in which the moistness is to be measured, the lowermost end of said branch being closed by a worm conveyor which is rotated intermittently by a motor.

* * * * *